US009226693B2

(12) United States Patent
Haas

(10) Patent No.: US 9,226,693 B2
(45) Date of Patent: Jan. 5, 2016

(54) CANINE GAIT ANALYZER

(71) Applicant: Clinical Image Retrieval Systems, Inc., Sparta, NJ (US)

(72) Inventor: Douglas D. Haas, Sparta, NJ (US)

(73) Assignee: Clinical Image Retrieval Systems, Inc., Sparta, NJ (US)

( * ) Notice: Subject to any disclaimer, the term of this patent is extended or adjusted under 35 U.S.C. 154(b) by 274 days.

(21) Appl. No.: 14/096,133

(22) Filed: Dec. 4, 2013

(65) Prior Publication Data

US 2014/0155786 A1 Jun. 5, 2014

Related U.S. Application Data

(60) Provisional application No. 61/733,225, filed on Dec. 4, 2012.

(51) Int. Cl.
*A61B 5/11* (2006.01)
*A61B 5/103* (2006.01)
*A61B 5/00* (2006.01)
*A63B 22/02* (2006.01)

(52) U.S. Cl.
CPC .............. *A61B 5/1038* (2013.01); *A61B 5/0077* (2013.01); *A61B 5/112* (2013.01); *A61B 2503/40* (2013.01); *A63B 22/0235* (2013.01)

(58) Field of Classification Search
CPC .. A61B 5/103; A61B 5/1036; A61B 5/10368; A61B 5/11; A61B 5/112; A61B 2503/00; A61B 2503/40; A63B 24/0087; A63B 24/009; A63B 24/0093; A63B 22/02; A63B 22/0235–22/0257

USPC ........ 119/700; 482/54; 601/35; 600/587, 592, 600/595

See application file for complete search history.

(56) References Cited

U.S. PATENT DOCUMENTS

| | | | | |
|---|---|---|---|---|
| 5,873,843 A * | 2/1999 | Draper | ................. | A61B 5/1038 600/595 |
| 7,572,206 B2 * | 8/2009 | Wilkins | ................... | A63B 5/00 482/8 |
| 8,002,672 B2 * | 8/2011 | Brunner | ............... | A61B 5/1038 482/54 |
| 2010/0056960 A1 * | 3/2010 | Lanny | ................... | A61B 5/1038 600/592 |
| 2014/0221160 A1 * | 8/2014 | Hardy | ................. | A61B 5/6895 482/8 |

* cited by examiner

*Primary Examiner* — Devin Henson
*Assistant Examiner* — David J McCrosky
(74) *Attorney, Agent, or Firm* — Hoffmann & Baron LLP

(57) ABSTRACT

A canine gait analyzer is used in connection with a treadmill. A sensor assembly includes a plurality of overlapping sensor panels, each having a pressure transducer array connected to a circuit board with conductive traces. An elastomer sheet with carbon-graphite dampens the dog's pawsteps, and is electrically grounded for static electric charge. The sensor assembly is held fast between the belt inner surface and the treadmill bed with a J bracket. The sensor panel edge extends downward on the side of the frame. A C-shaped side cover is attached to the frame and covers the sensor panel edge having the circuit boards. A motor speed controller is connected to the motor, the circuit boards, and to a computer.

20 Claims, 14 Drawing Sheets

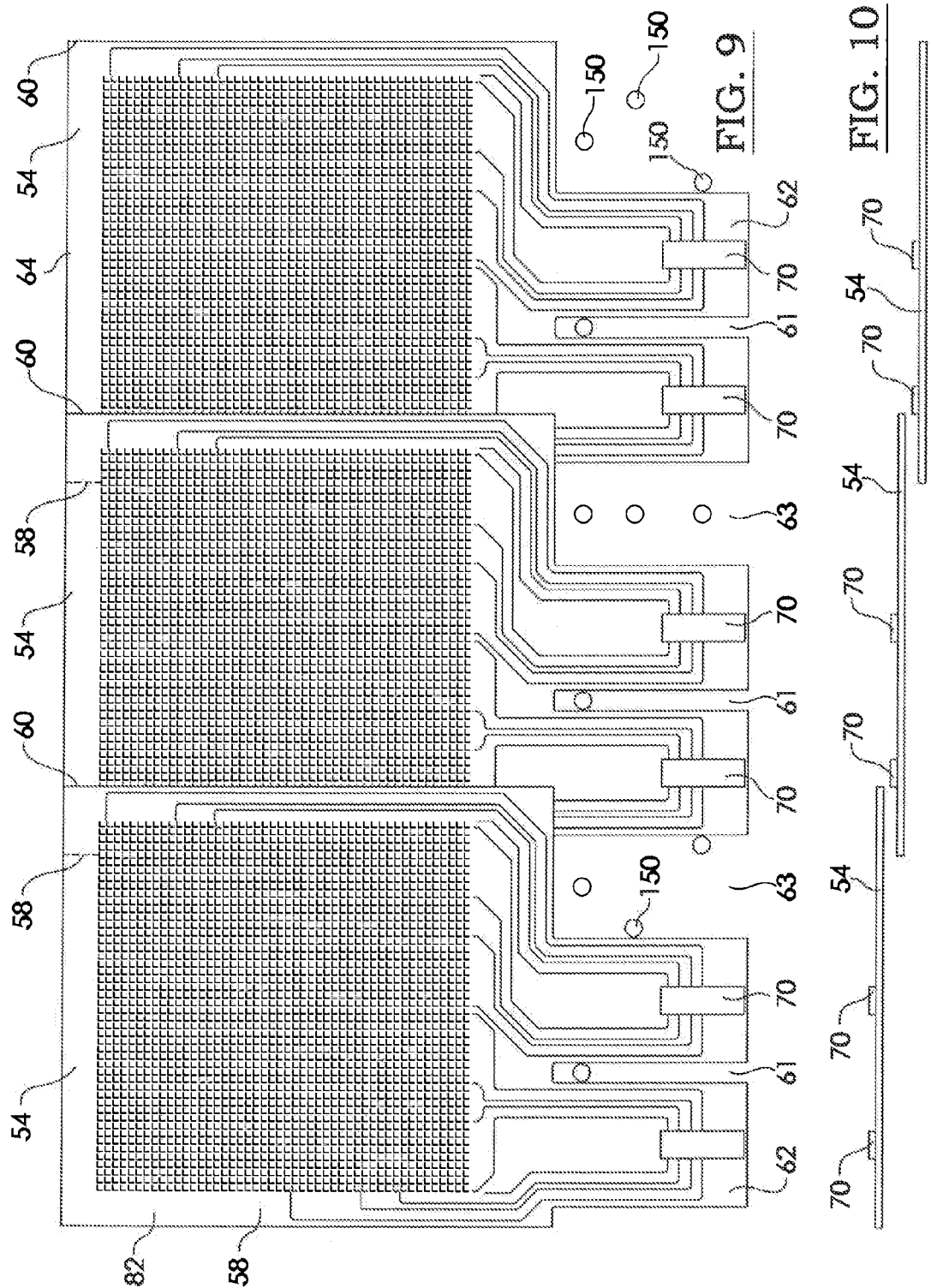

CANINE GAIT ANALYZER

CROSS-REFERENCE TO RELATED APPLICATIONS

Reference is hereby made to U.S. provisional application No. 61/733,225, entitled, "Canine Gait Analyzer," filed on 4 Dec. 2012, which is incorporated in its entirety for the teachings therein. Applicant hereby claims the benefit of the provisional filing date.

Reference is hereby made to software patent application entitled, "system and method to detect and quantify lameness in animals," which is incorporated in its entirety for the teachings therein.

INCORPORATION BY REFERENCE

U.S. Pat. No. 5,952,585, issued Sep. 14, 1999, entitled "Portable Pressure Sensing Apparatus For Measuring Dynamic Gait Analysis And Method Of Manufacture," is incorporated in its entirety for the teachings therein.

TECHNICAL FIELD

The presently disclosed technologies are directed generally to an apparatus and method for accurate identification of lameness in dogs, and in particular, to instrumentation that is adaptable to almost any industrial grade motorized dog treadmill, for analyzing primary and secondary lameness.

BACKGROUND

It is well known that dogs have an uncanny ability to compensate for an injured limb. A dog with a missing limb can maintain sufficient capability to keep up with a pack of healthy dogs. A dog with lameness in one leg can compensate so well that it is difficult, and sometimes impossible, to tell which leg is lame.

Current techniques used to identify lameness in a clinical setting are through visual observation, manual manipulation, x-ray and MRI test. The problem with these methods is the need to first determine which specific limb is the one that is manifesting either primary or secondary lameness. Experienced veterinary clinicians often fail to correctly identify the proper limb. It is reported that 1 in 5 dogs that enter a veterinary clinic have undetected lameness, and are therefore not treated. Until recently there were only three objective methods for identifying lameness. One was with expensive and time consuming 3D video. The other was by walking the dog in multiple passes over a force plate, and analyzing the data. Both of these methods are difficult to use and are highly inaccurate.

The third method is an over ground system using a long pressure sensor matrix laid under a carpeted walkway, which in recent years has proven to be highly accurate and easier to use in both research and clinical practice. While this method works well with humans in a clinical setting, it is less practical for use with dogs in clinical settings. In particular, the dog must walk at a constant, specified rate, and not stop, slow, or stray off the walkway.

Apparatus and methods for analyzing the gait of humans are known in the art. An example is disclosed in U.S. Pat. No. 5,952,585, the disclosure of which is incorporated herein by reference. While this system particularly relates to an over ground system for human patients, it has been adapted for use by four-legged animals, and specifically for use by dogs.

One way to overcome the problem of walking at a constant, specified rate is to utilize a treadmill. The treadmill can be adjusted to a specific rate of speed. The dog can be guided and controlled so as to walk centered on the treadmill. What is needed is to adapt the pressure sensor matrix apparatus, method, and software for use on a treadmill.

Accordingly there is a need to provide a canine gait analyzer that is user-friendly and that accurately identifies lameness without trained clinician expertise.

There is a further need to provide a canine gait analyzer of the type described and that works reliably for use with dogs in clinical settings.

There is a yet further need to provide a canine gait analyzer of the type described and which can be adapted for use on any commercially available treadmill, thereby avoiding the problems associated with the prior art.

There is a still further need to provide a canine gait analyzer of the type described and which can be manufactured at high quality in a cost-effective manner.

SUMMARY

In accordance with the present invention, there is disclosed a canine gait analyzer 20, for use in connection with a treadmill 22 having a frame 24, with opposite left 26 and right 28 sides. A bed 30 mounted on the frame 24, extends between a forward end 32 and a rear end 34, and has a top surface 36. A belt 42 having inner 44 and outer 46 surfaces is mounted on rollers 38 on the frame 24. A guardrail 48 is pivotally mounted on the frame 24, leaving a clear span between bushings 50 and 52. An alternative guardrail 148 is mounted on the frame 24 by upright stanchions 150.

A plurality of sensor panels 54 each having a portion of flexible material 56, extend between opposite front 58 and rear 60 ends, and between opposite left 62 and right 64 edges. The sensor panels 54 each have a pressure transducer array 66 received on the flexible material 56. Each sensor panel 54 has at least one circuit board 70 with electronic components adjacent either the left edge 62 or the right edge 64. Conductive traces 72 connect the pressure transducers 68 electrically to the circuit boards 70.

A sensor assembly 74 includes the plurality of sensor panels 54 adapted to be disposed in overlapping sequence from adjacent the bed forward end 32 to adjacent the bed rear end 34. An antifriction membrane 76 is stacked above the sensor panels 54, and allows the belt 42 to slide smoothly over the sensor assembly 74. The antifriction membrane 76 also holds the plurality of sensor panels 54 in proper spatial alignment and allows easy assembly onto the treadmill 22.

An elastomer sheet 78 is stacked either above or below the sensor panels 54. The disposition of the elastomer sheet 78, as well as the thickness and durometer, will be determined by the thickness of the belt, the weight of the dog, and the size of the dog's paws. The elastomer sheet 78 has carbon-graphite, so as to render the elastomer sheet conductive. The elastomer sheet 78 will be electrically grounded upon assembly to the treadmill 22 to ensure that any static electric charge will be bled to ground.

The sensor assembly 74 front end 82 is disposed adjacent the bed forward end 32. The sensor assembly 74 is installed between the belt inner surface 44 and the bed 30, and lies generally flat upon the bed top surface 36. The sensor panel edge having the circuit boards 70 extends outward and downward on the side of the frame 24. The sensor assembly 74 extends underneath the frame 24 with the circuit boards 70 disposed beneath the frame 24. In an alternate embodiment, the sensor assembly 274 extends downward alongside the frame 24, and then curves upward with the circuit boards 70 disposed alongside the frame 24.

Tape or adhesive (not shown) is used for attaching the antifriction membrane 76 and the elastomer sheet 78 to the sensor panels 54. The sensor assembly 74 is attached to the treadmill 22 with a J bracket 84, which is adapted to extend across the bed forward end 32. Thus, the belt 30 will pass over the sensor assembly 74 and the J bracket 84 without moving the sensor assembly 74 with respect to the bed 30.

A side cover 100 is generally C-shaped in cross-section, and is adapted to be attached to one of the frame left 26 and right 28 sides. The side cover 100 covers the sensor panel edge having the circuit boards 70. The side cover will enclose, support and protect the sensor panel edges 62 or 64, and the circuit boards 70. In FIG. 1, the circuit boards 70 are attached on the sensor panel left edge 62. The sensor panels 54 and the circuit boards 70 can be attached on the sensor panel right edge 64 and project out the frame right side 28.

A computer 112 is connected to the circuit boards 70. A motor speed controller 114 is connected to the motor (not shown) and to the computer 112. The circuit boards 70 are connected together.

Upon assembling the canine gait analyzer 20 to the treadmill 22, the sensor assembly 74 will be installed by sliding transversely between the belt inner surface 44 and the bed top surface 36. The J bracket 84 will engage the bed forward end 32. The sensor assembly 74 will lie generally flat upon the bed top surface 36. The elastomer sheet 78 will be connected to the electrical ground 80, so as to bleed any static electrical charge to ground. The computer 112 will be connected to the circuit boards 70, and the motor speed controller 114 will be connected to the motor and to the computer 112.

These and other aspects, objectives, features, and advantages of the disclosed technologies will become apparent from the following detailed description of illustrative embodiments thereof, which is to be read in connection with the accompanying drawings.

BRIEF DESCRIPTION OF THE DRAWINGS

FIG. 9 is a top plan view of several sensor array panels of FIGS. 1-7, overlapping one another in a first overlap pattern.

FIG. 10 is a side elevational view of the sensor array panels of FIG. 9, showing the overlap pattern.

In FIGS. 1-7, the perspective is from the front looking toward the rear of the treadmill. The left and right aspects are established looking from the rear toward the front. Hence, the treadmill frame left side is on the right of the figure.

DETAILED DESCRIPTION

Figure 1:
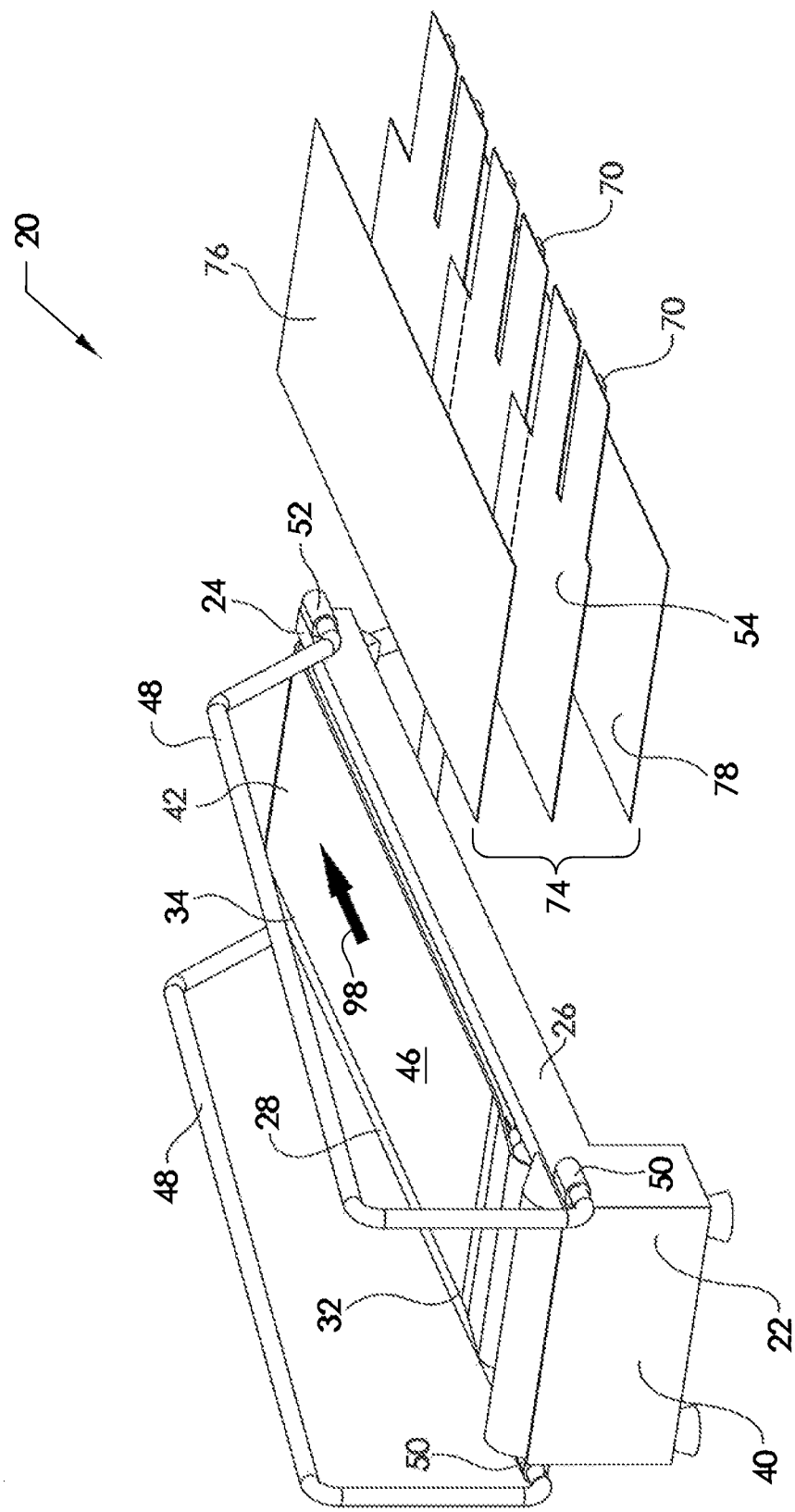
FIG. 1 is a perspective view of a canine gait analyzer constructed in accordance with the invention, mounted on a generic treadmill, and showing the sensor panels exploded apart and away from the treadmill.

Describing now in further detail these exemplary embodiments with reference to FIGS. 1-4 as described above, a canine gait analyzer is shown at 20, and is for use in connection with a treadmill 22. The treadmill 22 has a frame 24, with opposite left 26 and right 28 sides. The treadmill 22 has a treadmill forward end 40. A bed 30 is mounted on the frame 24, the bed 30 extending between a forward end 32 and a rear end 34. The bed 30 has a top surface 36. Front and rear rollers 38 are mounted on the frame 24. A belt 42 is mounted on the rollers 38. A motor (not shown) drives one of the rollers. The belt 42 has inner 44 and outer 46 surfaces. A guardrail 48 is mounted on the frame 24 at front 50 and rear 52 pivotal bushings. The guardrail 48 is thereby able to be pivoted downward onto the bed for storage. This leaves a clear span between the bushings 50 and 52.

Figure 8:
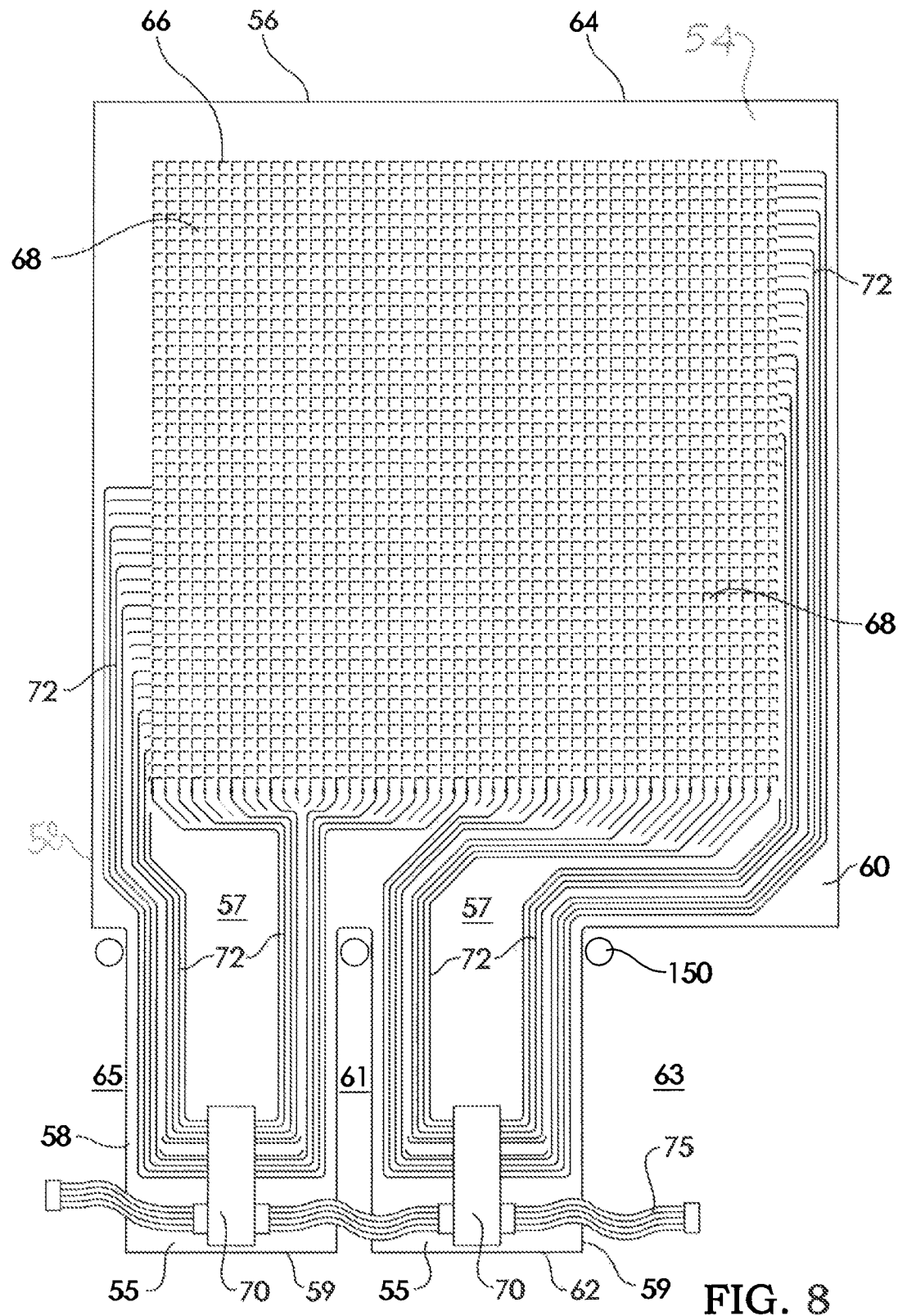
FIG. 8 is a top plan view of a typical sensor array panel of the canine gait analyzer of FIGS. 1-7.
Figures 11, 12:
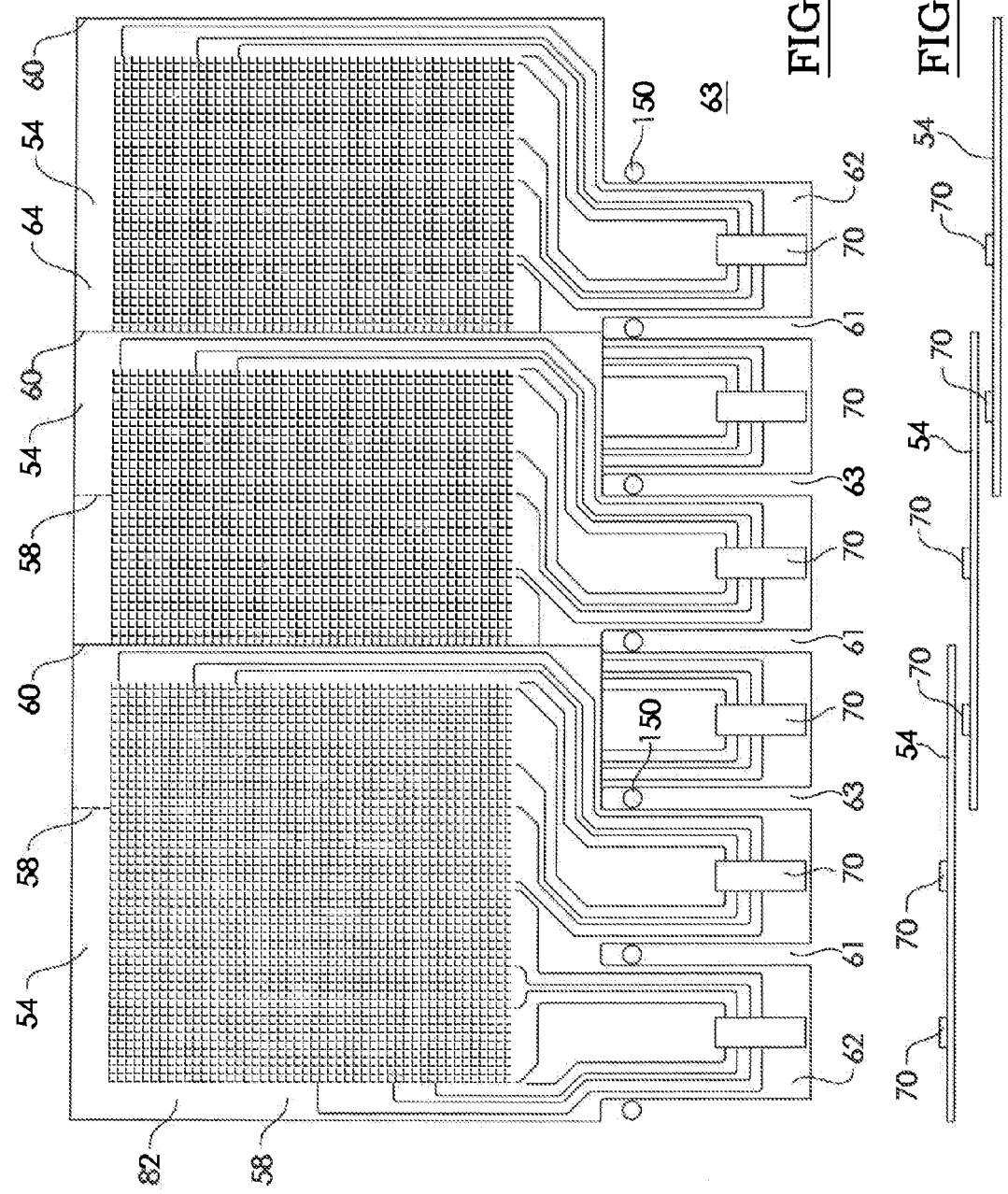
FIG. 11 is a top plan view of several sensor array panels of FIGS. 1-7, overlapping one another in a second overlap pattern.
FIG. 12 is a side elevational view of the sensor array panels of FIG. 11, showing the overlap pattern.

At least one, and typically a plurality of sensor panels 54 are employed, as shown in FIG. 8. The sensor panels 54 each have a portion of flexible material 56, and extend between opposite front 58 and rear 60 ends, and between opposite left 62 and right 64 edges. The sensor panels 54 each have a pressure transducer array 66 received on the flexible material 56. The transducer array 66 has a plurality of pressure transducers 68 arranged in an orthogonal matrix. Each one of the plurality of sensor panels 54 has at least one circuit board 70 adjacent either the left edge 62 or the right edge 64. Each circuit board 70 includes electronic components (not shown). Each sensor panel 54 has conductive traces 72 connecting the pressure transducers 68 electrically to the circuit boards 70. Each sensor panel 54 includes two peninsular portions 55 extending outward from a proximal end 57 adjacent one of the left and right edges to a distal end 59, the peninsular portions 55 being separated by a first cutout region 61. A second cutout region 63 is adjacent one of the peninsular portions, the second cutout region 63 extending outward from the peninsular portion proximal end 57 adjacent one of the left and right edges to the peninsular portion distal end 59. The second cutout region 63 extends from one of the front 58 and rear 60 ends to one of the peninsular portions 55. An optional third cutout region 65 is adjacent the front end 58. Typically, two circuit boards 70 are provided, each circuit board 70 being mounted on one of the peninsular portions 55. The purpose of the cutout regions 61 and 63 and 65 is to clear the upright stanchions 150 on the type of treadmill 122 as described below in greater detail. Notice that the amount of overlap between the panels can vary, thereby varying the space between panels. FIGS. 11 & 12 show closely spaced panels. FIGS. 9 & 10 show wider spacing to accommodate the center to center distances between the upright stanchions 150.

Figure 16:
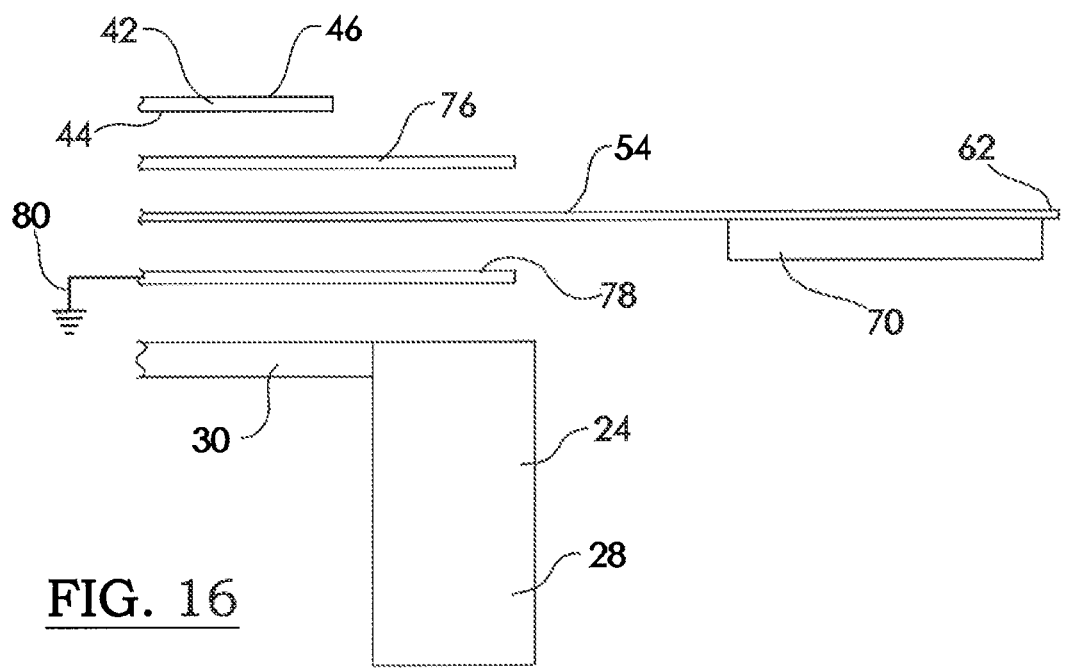
FIG. 16 is a front elevational, cross-sectional, exploded view of a first sensor assembly of the canine gait analyzer of FIG. 1, taken across lines 16-16 of FIG. 3.
Figure 17:
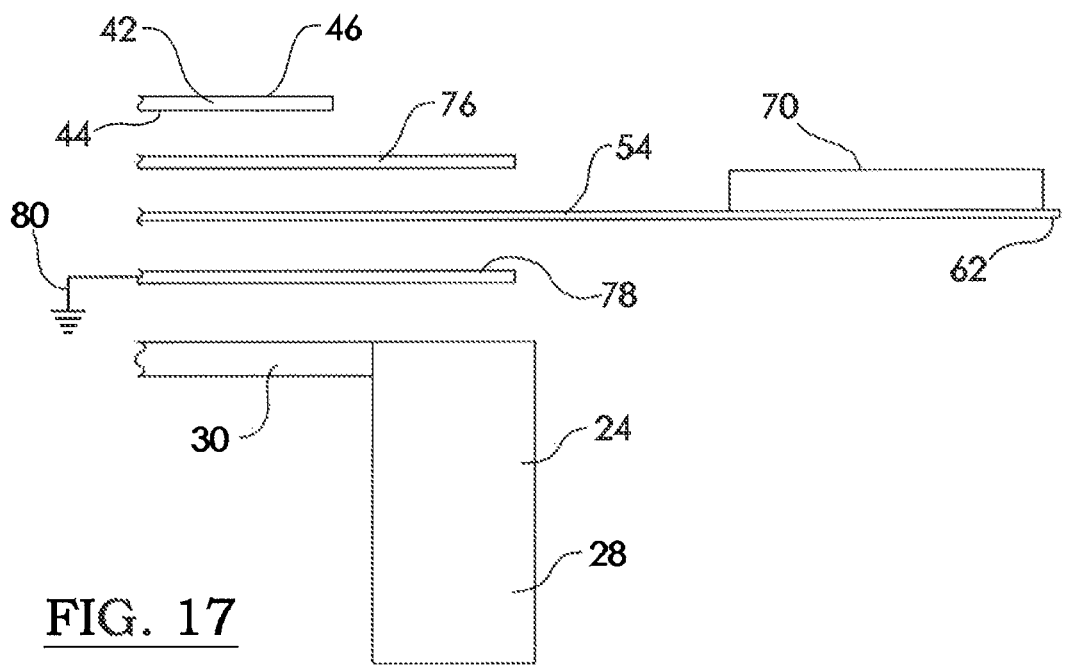
FIG. 17 is a front elevational, cross-sectional, exploded view of a second sensor assembly of the canine gait analyzer of FIG. 1, taken across lines 17-17 of FIG. 7.
Figure 18:
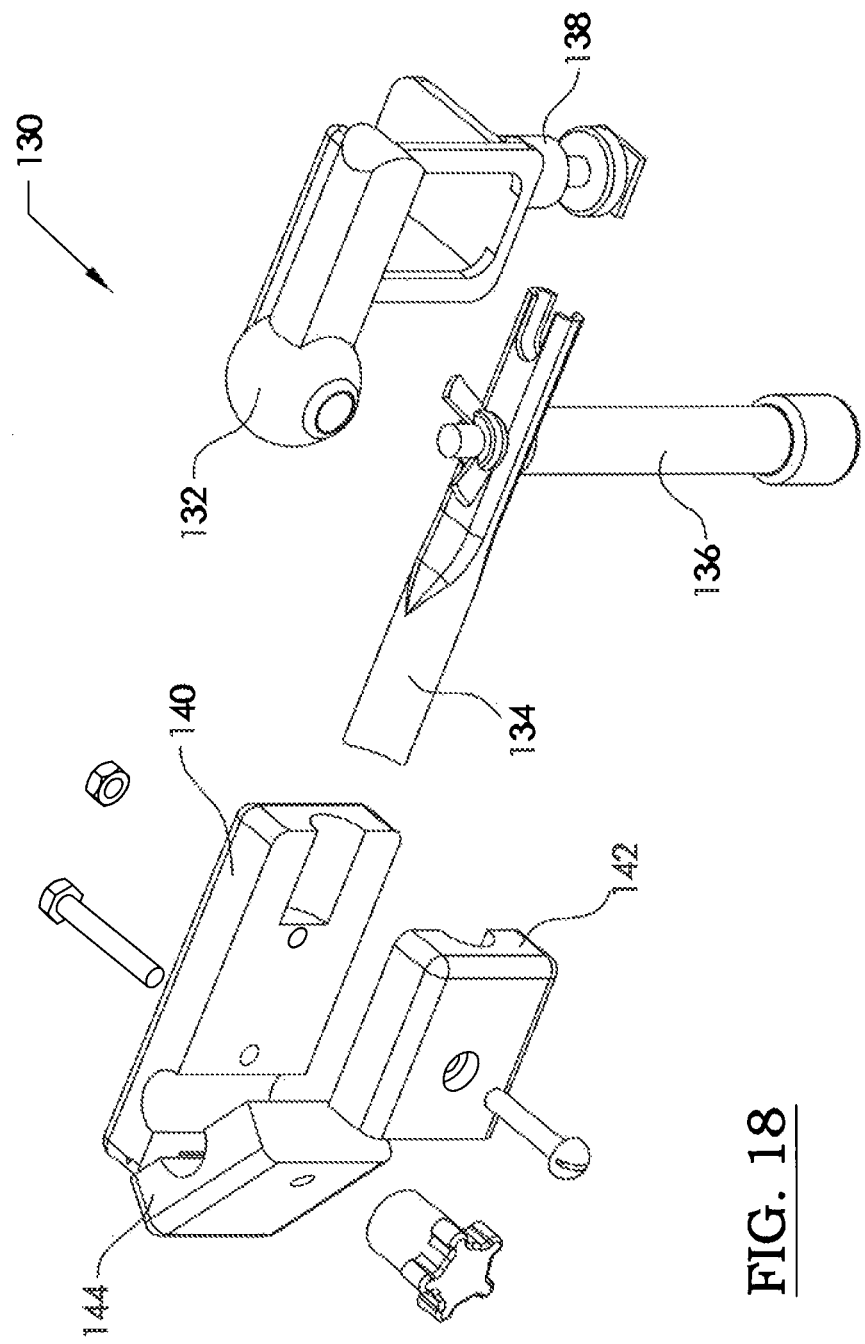
FIG. 18 is a perspective view of a camera and a camera mounting bracket.

A sensor assembly 74 includes a plurality of sensor panels 54 adapted to be disposed in overlapping sequence from adjacent the bed forward end 32 to adjacent the bed rear end 34, as shown in FIGS. 9-12. An antifriction membrane 76 is stacked above the sensor panels 54, as shown in FIGS. 16 and 17. The antifriction membrane 76 allows the belt 42 to slide smoothly over the sensor assembly 74 without dislodging or moving the sensor assembly 74. The antifriction membrane 76 also holds the plurality of sensor panels 54 in proper spatial alignment and allows easy assembly onto the treadmill 22. The antifriction membrane 76 can be made of, for example, polyester Melanex®, or similar polymeric material having a low coefficient of friction and good tensile strength.

An elastomer sheet 78 is stacked adjacent the sensor panels. The elastomer sheet 78 is typically disposed below the sensor panels 54 as shown in FIGS. 16 & 17. The antifriction membrane 76 is preferably above the elastomer sheet 78 as shown in FIGS. 16 & 17, so as to protect the sensor assembly 74 from the friction of the moving belt 42. The disposition of the elastomer sheet 78, as well as the thickness and durometer, will be determined by the thickness of the belt, the weight of the dog, and the size of the dog's paws, as determined empirically. The elastomer sheet 78 has carbon-graphite compounded along with the elastomer material, so as to render the elastomer sheet at least partly conductive. The elastomer sheet 78 will be electrically grounded upon assembly to the treadmill 22. The ground 80 ensures that any static electric charge will be bled to ground, so as not to damage the electronic components.

Figure 14:
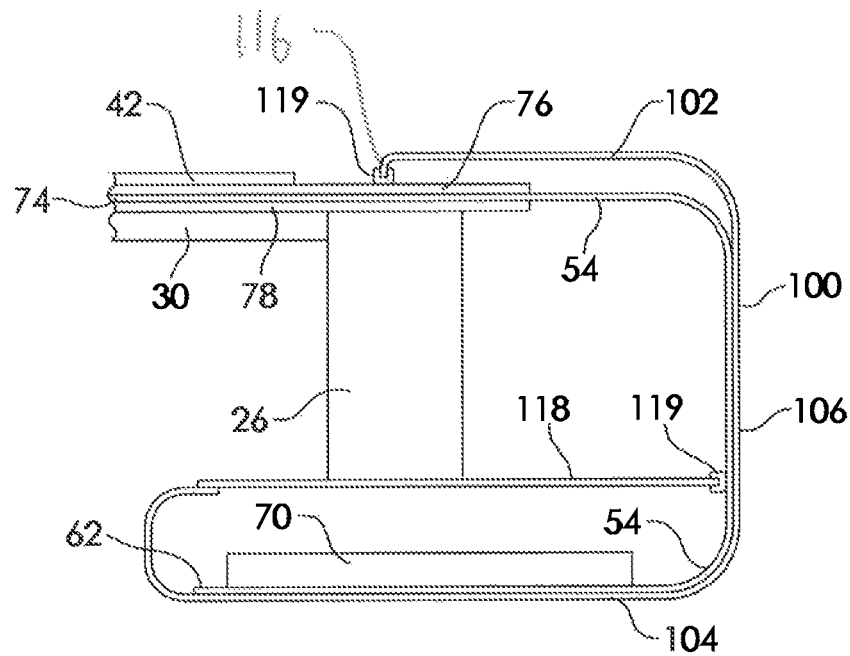
FIG. 14 is a front elevational, cross-sectional view of the sensor assembly and side cover of the canine gait analyzer of FIG. 1, taken across lines 14-14 of FIG. 4.

The sensor assembly 74 has a front end 82 disposed adjacent the bed forward end 32. The sensor assembly 74 is adapted for installation between the belt inner surface 44 and the bed 30, as shown in FIGS. 16 & 17. The sensor assembly 74 is adapted to lie generally flat upon the bed top surface 36, with the one of the left and right sensor panel edges having the circuit boards 70 extending outward and downward on the respective side of the frame 24. The sensor assembly 74 extends underneath the frame 24 with the circuit boards 70 disposed beneath the frame 24, as shown in FIG. 14. FIGS. 1-7 show the sensor panel edge having the circuit boards 70 extending outward on the left side of the treadmill 22 (left side looking from the rear to the front). The sensor panel edges can be on either the right side 28, or the left side 26 as shown in FIG. 1.

Figure 2:
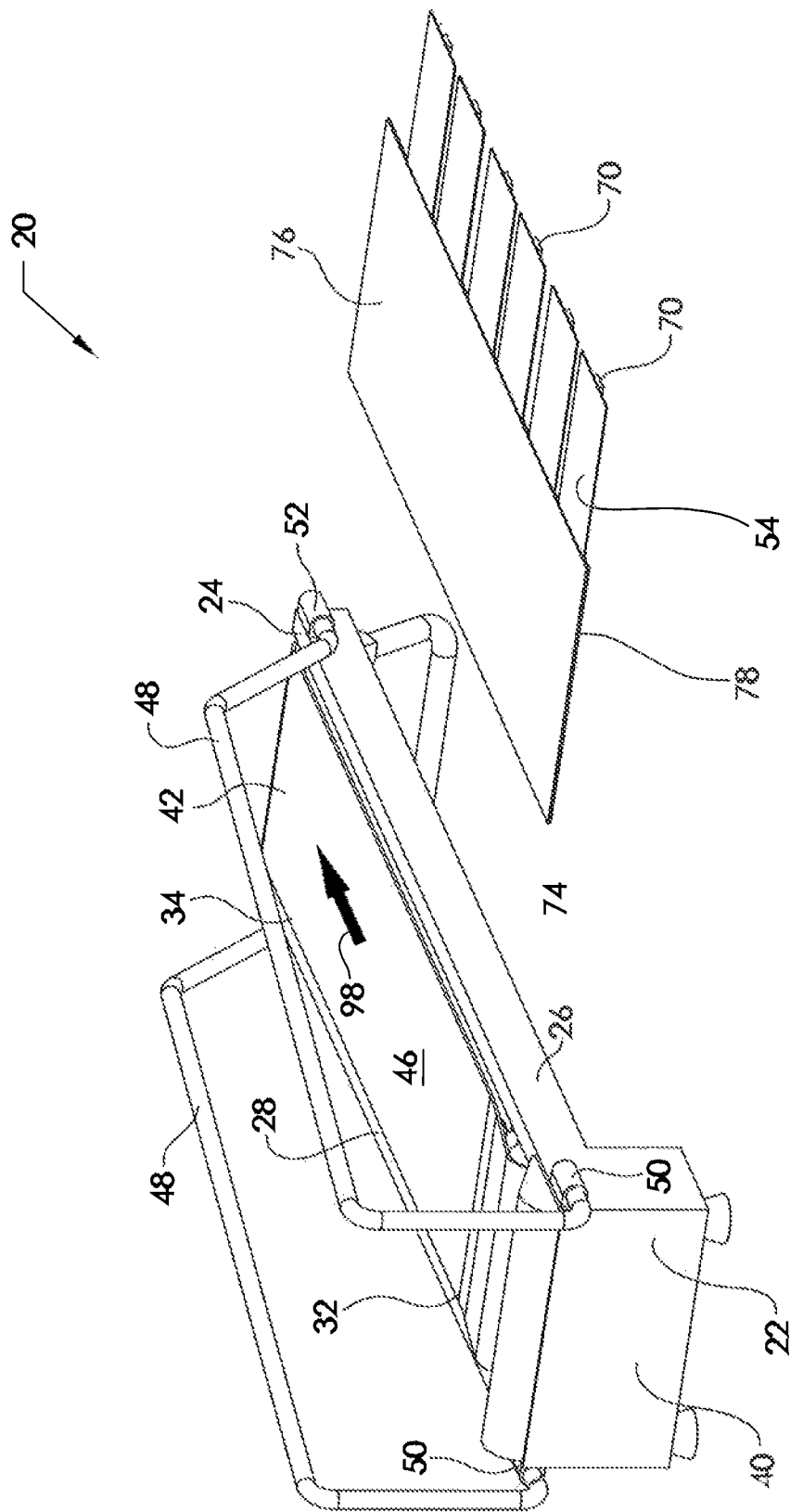
FIG. 2 is a perspective view of the canine gait analyzer of FIG. 1, and showing the sensor panels contracted and away from the treadmill.
Figure 3:
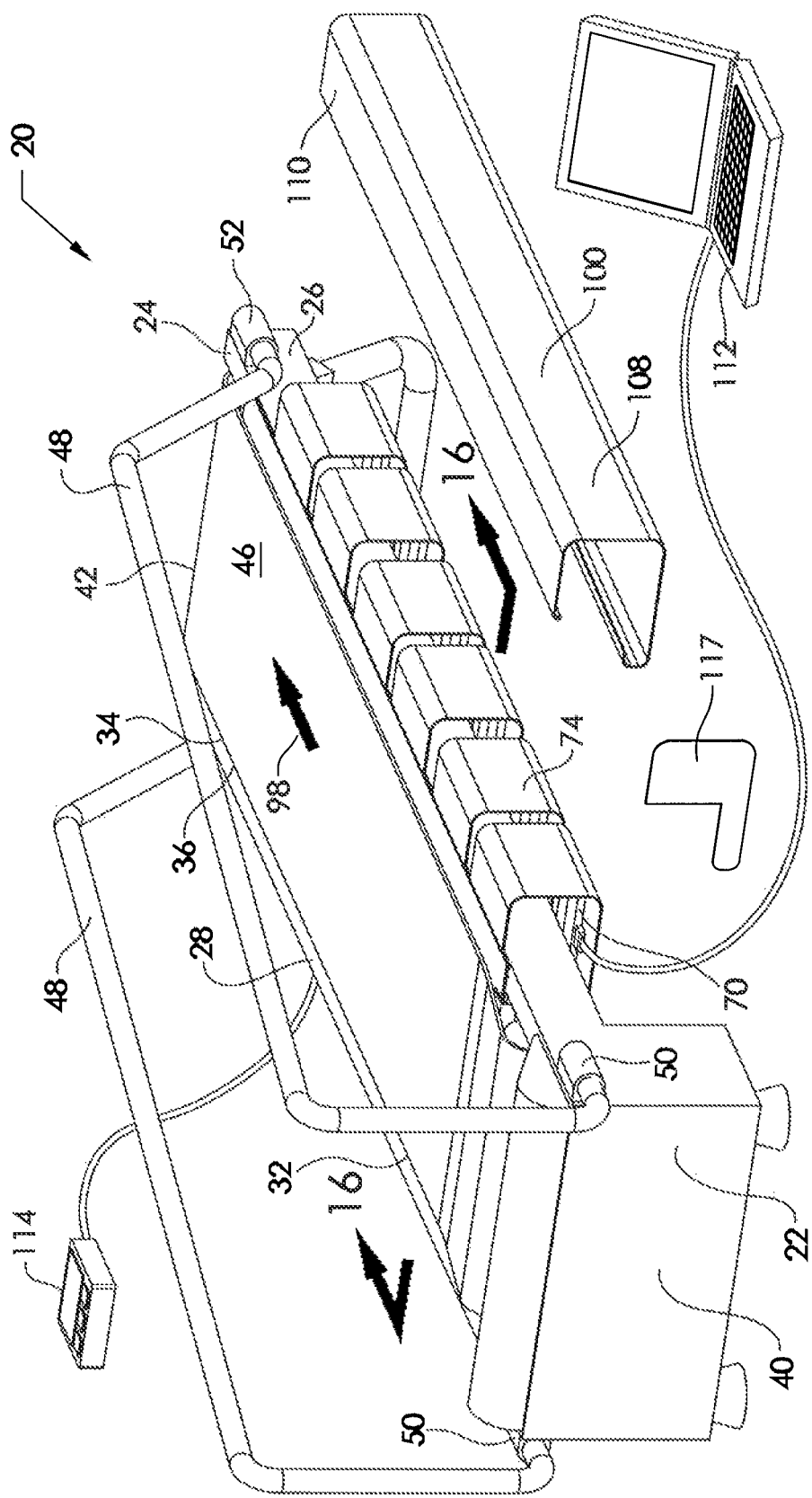
FIG. 3 is a perspective view of the canine gait analyzer of FIG. 1, showing the sensor panels installed on the treadmill with the circuit boards underneath the treadmill, and showing the side cover exploded away from the treadmill.
Figure 4:
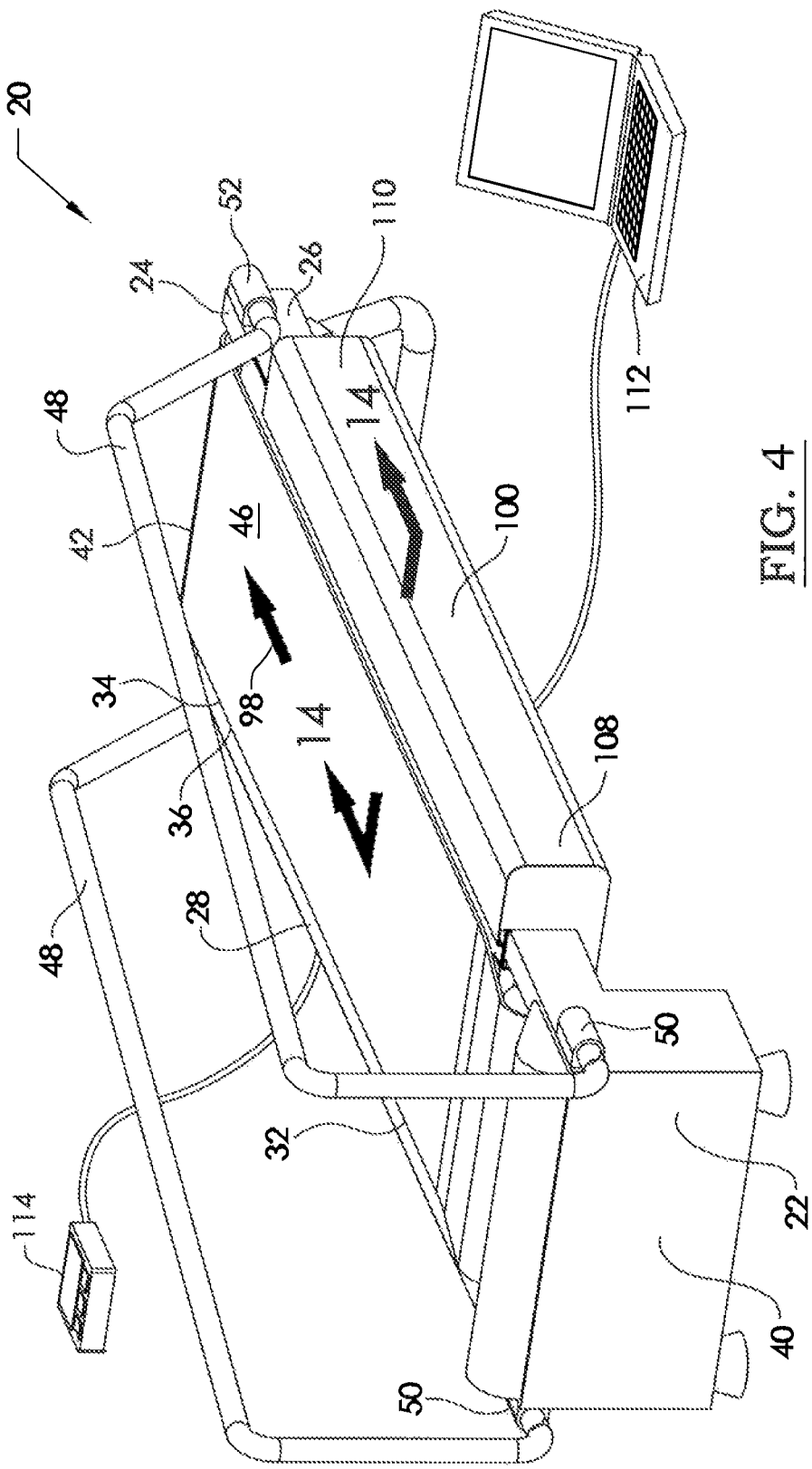
FIG. 4 is a perspective view of the canine gait analyzer of FIG. 1, fully assembled.

The assembly sequence is shown in FIGS. 1-4. In FIG. 1, the three layers are stacked and ready for assembly. FIG. 2 shows the three layers sandwiched together. FIG. 3 has the sensor assembly 74 installed in the treadmill between the bed 30 and the belt 42, with the peninsular portions 55 extending downward and underneath the treadmill. FIG. 4 shows the completed assembly.

Attaching means, specifically tape or adhesive (not shown), is provided for attaching the antifriction membrane 76 and the elastomer sheet 78 to the sensor panels 54.

Figure 13:
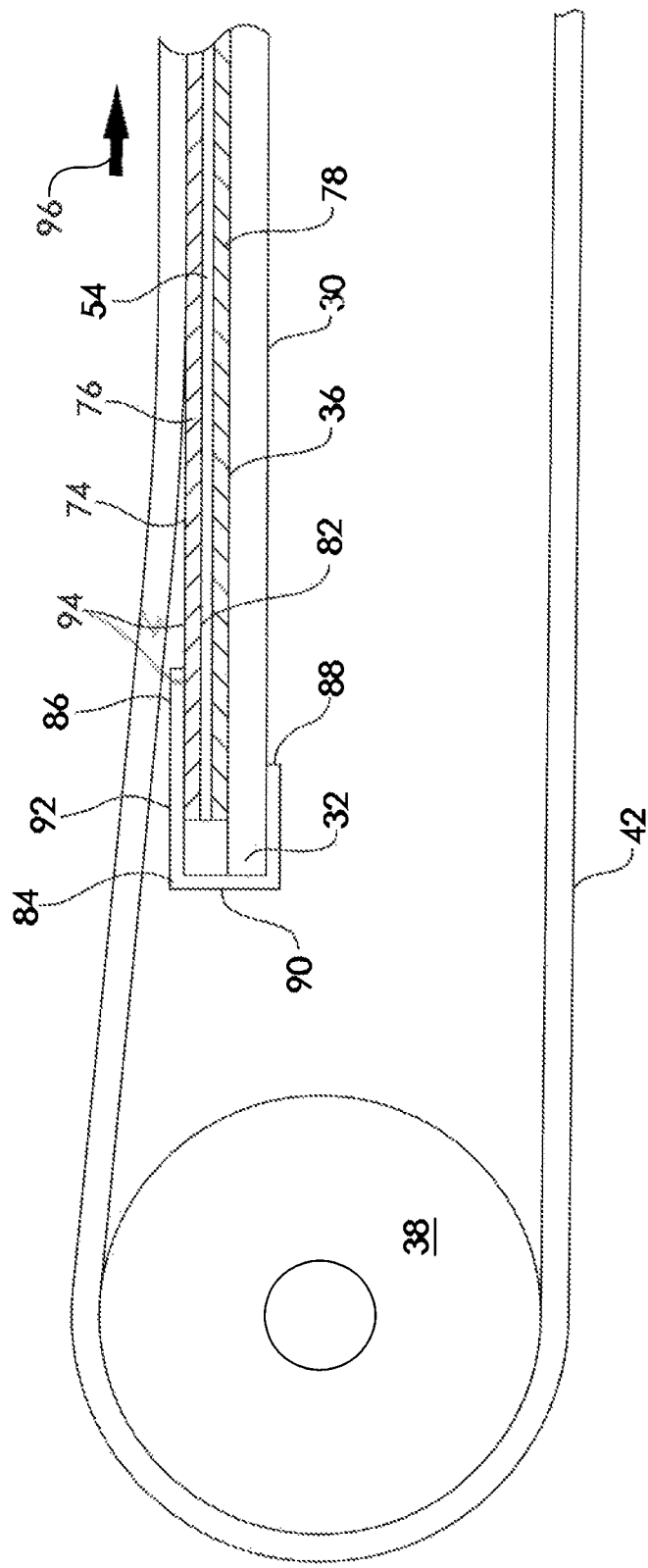
FIG. 13 is a side elevational, cross-sectional view of a J-bracket holding the sensor assembly onto the front of the treadmill bed, taken across lines 13-13 of FIG. 5.

An attaching member is provided for attaching the sensor assembly 74 to the bed 30. Specifically, a J bracket 84 as shown in FIG. 13, has an upper flange 86 and a lower flange 88 connected by a web 90. The upper flange 86 has opposite top 92 and bottom 94 surfaces. The J bracket 84 is adapted to extend across the bed forward end 32 with the upper flange 86 above the bed 30 and the lower flange 88 below the bed 30 and the web 90 adjacent the bed forward end 32. The belt 42 passes over the upper flange top surface 92 in the direction shown by arrow 96. The sensor assembly 74 is attached to the upper flange bottom surface 94, so that the J bracket 84 will hold the sensor assembly 74 disposed on the bed 30 with the sensor assembly front end 82 adjacent the bed forward end 32. Thus, the belt 30 will pass over the sensor assembly 74 without moving the sensor assembly 74 with respect to the bed 30.

A side cover 100, shown in FIG. 14, has an upper flange 102 and a lower flange 104 connected by a web 106. The lower flange 104 is bent upward at the inside edge. The side cover 100 is generally C-shaped in cross-section, and extends between opposite front 108 and rear 110 ends. The side cover 100 is adapted to be attached to one of the frame left 26 and right 28 sides. The side cover 100 is adapted to cover the one of the left 62 and right 64 sensor panel edges having the circuit boards 70. The side cover lower flange 104 extends underneath the treadmill frame 24 to enclose, support and protect the sensor panel edges 62 or 64, and the circuit boards 70. In FIG. 3, the circuit boards 70 are attached on the sensor panel left edge 62. It is understood that the sensor panels 54 can be inverted so that the circuit boards 70 are attached on the sensor panel right edge 64 and project out the frame right side 28. The side cover upper flange 102 includes a ridge 116 extending from the front 108 to the rear 110 end and projecting downward. The ridge 116 serves to hold down the edge of the sensor assembly 74 and to seal against RF (radio frequency) emissions. The ridge can have an optional gasket 119. A seal plate 118 extends from the inside edge of the lower flange 104 across to the inside of the web 106, as shown in FIG. 14. The seal plate 118 extends from the front 108 to the rear 110 end of the side cover 100. The seal plate 118 shields any spurious RF emissions from escaping. A gasket 119 allows the seal plate 118 to gently press against the sensor panels 54 without cutting into them. An end plate 117 on each end 108, 110, of the side cover 100 completes the RF shield. Only the front end plate 117 is shown in FIGS. 3-7, the rear end plate is not shown, but is similar and opposite-hand. Threaded fasteners (not shown) attach the side cover 100, seal plate 118, and end plates 117 to the frame side 26 or 28, and ensure electrical continuity. This type of side cover 100 is preferred, as it places the circuit boards 70 underneath the treadmill, and less susceptible to damage.

Figure 15:
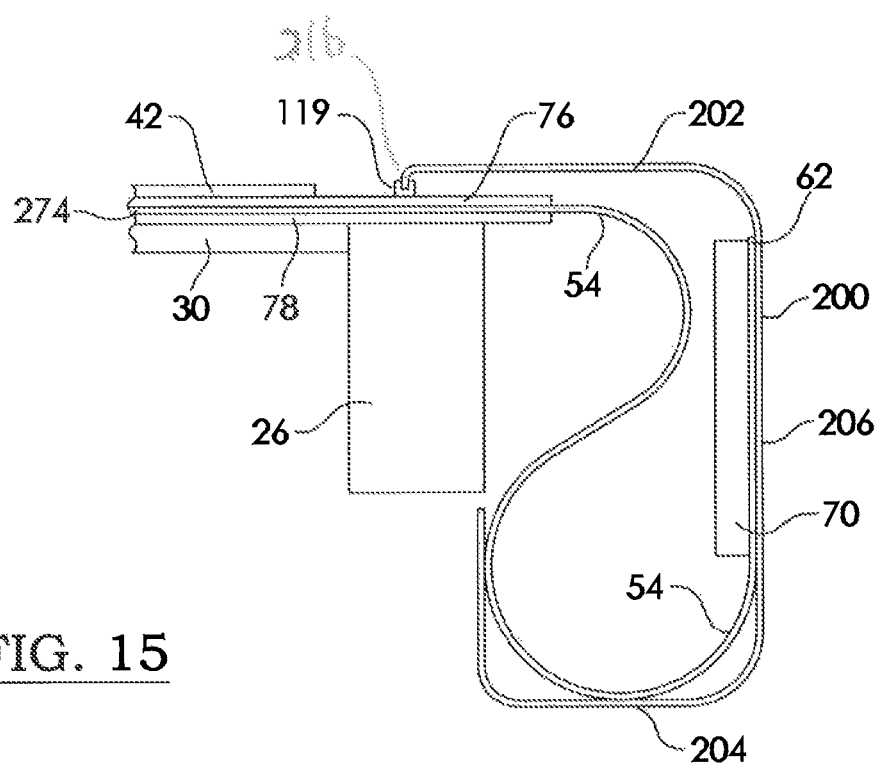
FIG. 15 is a front elevational, cross-sectional view of the sensor assembly and side cover of the canine gait analyzer of FIG. 5, taken across lines 15-15 of FIG. 6.

An alternative side cover 200, shown in FIG. 15, has an upper flange 202 and a lower flange 204 connected by a web 206. The lower flange 204 is bent upward at the inside edge. The side cover 200 is generally C-shaped in cross-section, and extends between opposite front 208 and rear 210 ends. The side cover 200 is adapted to be attached to one of the frame left 26 and right 28 sides. The side cover 200 is adapted to cover the one of the left 62 and right 64 sensor panel edges having the circuit boards 70. The side cover lower flange 204 extends underneath the treadmill frame 24 to enclose, support and protect the sensor panel edges 62 or 64, and the circuit boards 70. The side cover upper flange 202 includes a ridge 116 extending from the front 208 to the rear 210 end and projecting downward. The ridge 216 serves to hold down the edge of the sensor assembly 74 and to seal against RF (radio frequency) emissions. The ridge can have an optional gasket 119. This type of side cover 200 is employed where an obstruction is found under the treadmill that precludes placement of the circuit boards 70 there.

A computer 112 is adapted to be connected to the circuit boards 70. A motor speed controller 114 is adapted to be connected to the motor (not shown) and to the computer 112. The circuit boards 70 are connected together with flat ribbon cable 75, as shown in FIG. 8.

A camera mounting bracket 130 is provided for attaching a video camera 132 so as to record the diagnostic session. The camera mounting bracket 130 includes a clamp base 140, a clamp block 142, and a clamp jaw 144, for attachment to the upright stanchions 150 or the guardrail 48, 148. An arm 134 receives the clamp on one end. A ball head 138 is mounted on the opposite end of the arm 134. The camera 132 is attached to the ball head 138 in the usual manner.

Thus, upon assembling the canine gait analyzer 20 to the treadmill 22, the sensor assembly 74 will be installed by sliding transversely between the belt inner surface 44 and the bed top surface 36. The J bracket 84 will engage the bed forward end 32. The sensor assembly 74 will lie generally flat upon the bed top surface 36. The elastomer sheet 78 will be connected to the electrical ground 80, so as to bleed any static electrical charge to ground. The computer 112 will be connected to the circuit boards 70, and the motor speed controller 114 will be connected to the motor and to the computer 112.

Figure 5:
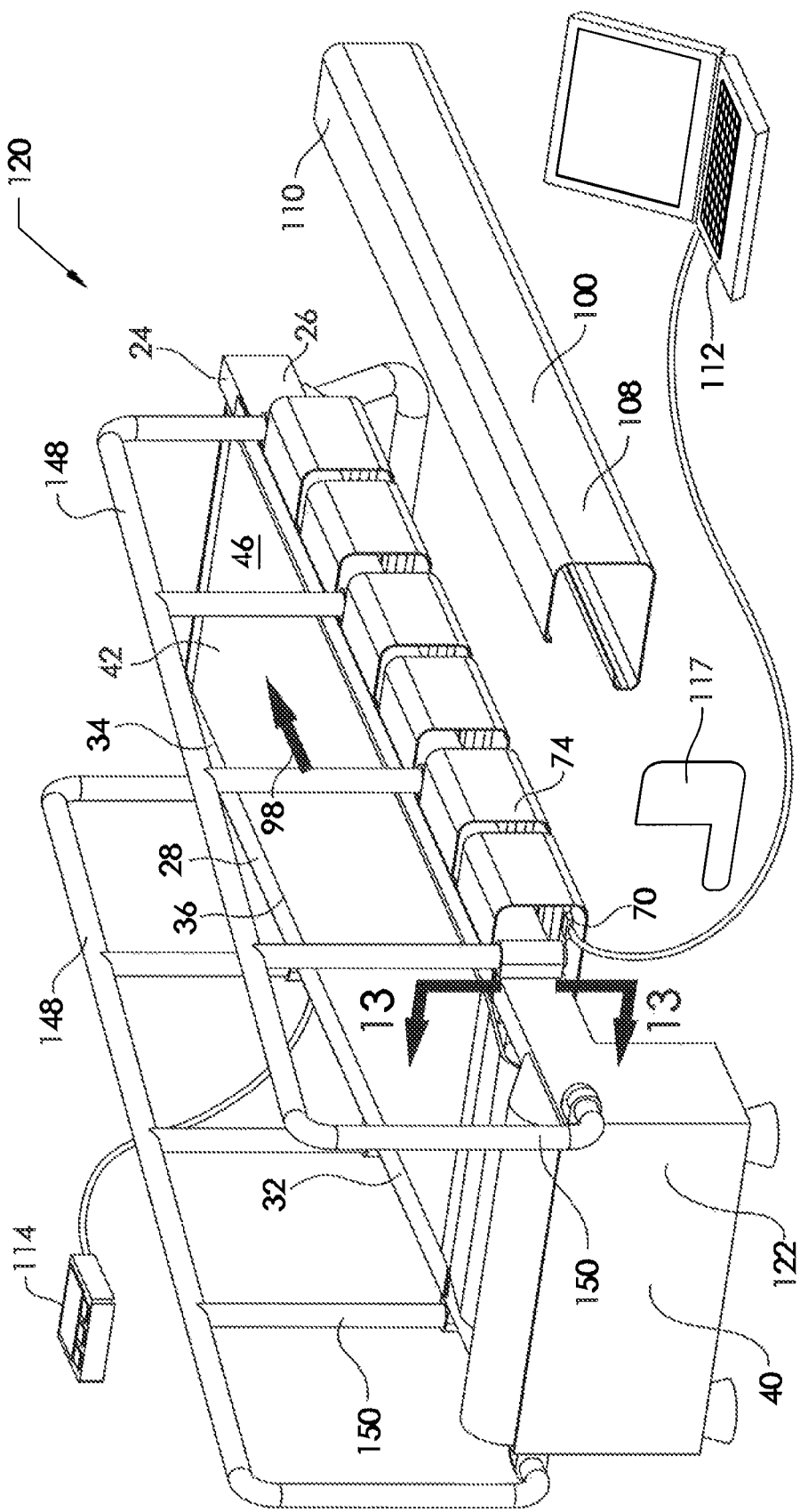
FIG. 5 is a perspective view of the canine gait analyzer of FIG. 1, mounted on another generic treadmill, and showing the sensor panels installed on the treadmill with the circuit boards underneath the treadmill, and the side cover exploded away from the treadmill.

Referring now to FIG. 5, a canine gait analyzer is shown at 120, and is similar to the canine gait analyzer 20 described above, in that canine gait analyzer 120 is used in connection with a treadmill 122. The treadmill 122 is similar to treadmill 22 described above in that it has a frame 24, with opposite left 26 and right 28 sides. The treadmill 122 has a treadmill forward end 40. A bed 30 is mounted on the frame 24, the bed 30 extending between a forward end 32 and a rear end 34. The bed 30 has a top surface 36. Front and rear rollers 38 are mounted on the frame 24. A belt 42 is mounted on the rollers 38. A motor (not shown) drives one of the rollers. The belt 42 has inner 44 and outer 46 surfaces. The treadmill 122 differs from treadmill 22 in that a guardrail 148 is mounted on the frame 24 by upright stanchions 150. The guardrail 148 is installed and removed vertically. This leaves no clear span along the left 26 and right 28 sides of the frame 24.

Typically, a plurality of sensor panels 54 are employed, as shown in FIG. 8, and described above. The purpose of the cutout regions 61 and 63 and 65 is to clear the upright stanchions 150 on this type of treadmill 122. Notice that the amount of overlap between the panels can vary, thereby varying the space between panels. FIGS. 11 & 12 show closely spaced panels. FIGS. 9 & 10 show wider spacing to accommodate the center to center distances between the upright stanchions 150.

A sensor assembly 74 includes a plurality of sensor panels 54 adapted to be disposed in overlapping sequence from adjacent the bed forward end 32 to adjacent the bed rear end 34, as shown in FIGS. 9-12. The sensor assembly 74 is adapted to lie generally flat upon the bed top surface 36, with the one of the left and right sensor panel edges having the circuit boards 70 extending outward and downward on the respective side of the frame 24. The sensor assembly 74 extends underneath the frame 24 with the circuit boards 70 disposed beneath the frame 24, as described above and shown in FIG. 14.

The J bracket 84 and the side cover 100 are the same as for canine gait analyzer 20 described above. A computer 112 is adapted to be connected to the circuit boards 70. A motor speed controller 114 is adapted to be connected to the motor (not shown) and to the computer 112. The circuit boards 70 are connected together in a similar manner to canine gait analyzer 20.

Assembling the canine gait analyzer 120 to the treadmill 122 is similar to the procedure described above, except that the two peninsular portions 55 of each sensor panel 54 will straddle one of the upright stanchions 150.

Figure 6:
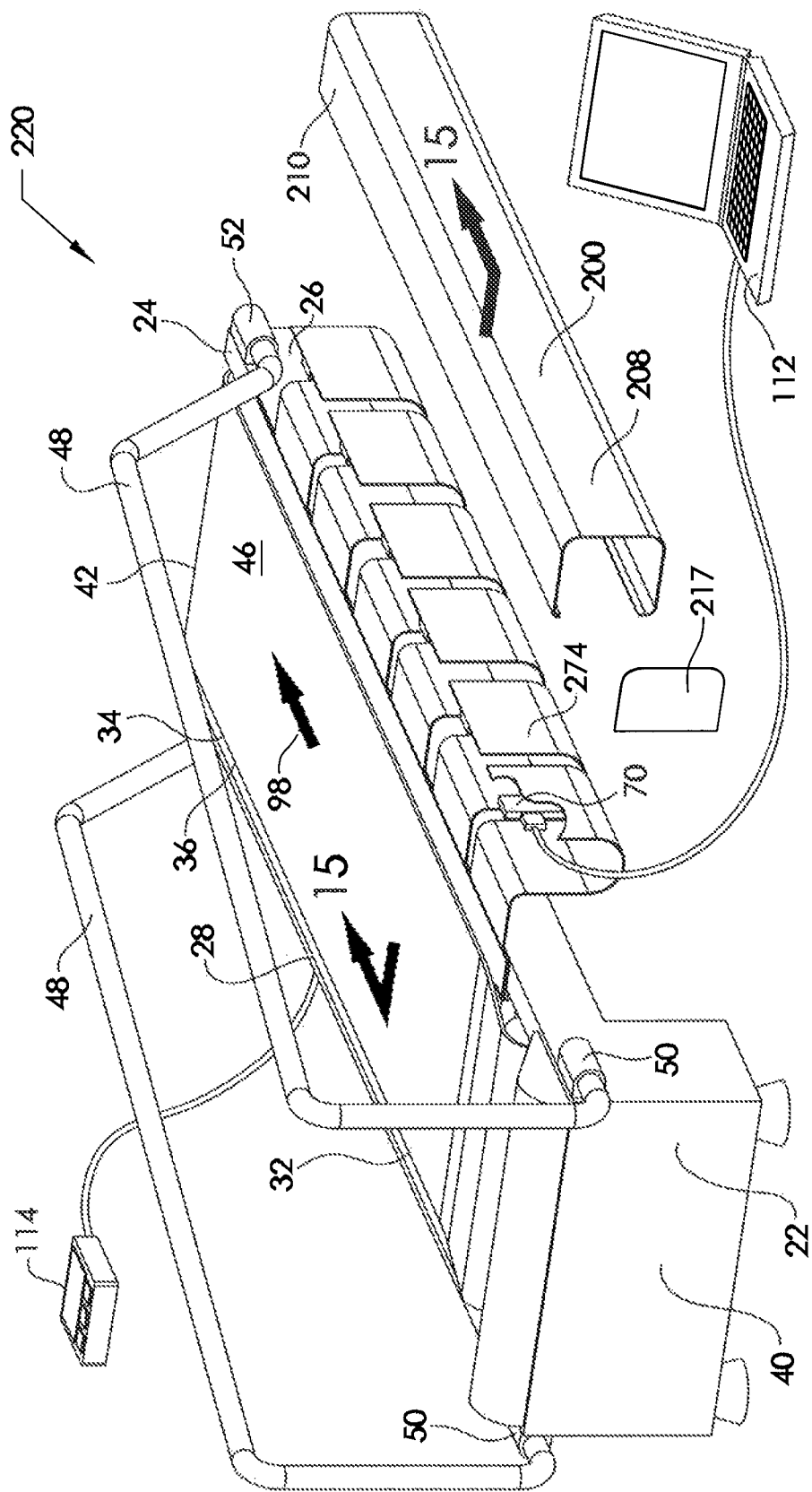
FIG. 6 is a perspective view of the canine gait analyzer of FIG. 1, mounted on the treadmill of FIG. 1, and showing the sensor panels installed on the treadmill with the circuit boards alongside the treadmill, and the side cover exploded away from the treadmill.

Turning now to FIG. 6, a canine gait analyzer is shown at 220, and is similar to the canine gait analyzer 20 described above, in that canine gait analyzer 220 is used in connection with the treadmill 22 as described above. Treadmill 22 has a guardrail 48 mounted on the frame 24 at front 50 and rear 52 pivotal bushings. The guardrail 48 is thereby able to be pivoted downward onto the bed for storage. This leaves a clear span between the bushings 50 and 52.

Typically, as before, a plurality of sensor panels 54 are employed, as shown in FIG. 8. The peninsular portions 55 and cutout regions 61 and 63 and 65 of the sensor panels 54 are not needed, and are optional. They are shown so that a common subassembly modular construction can be employed for economical manufacture.

A sensor assembly 274 is similar to sensor assembly 74 in that sensor assembly 274 includes the plurality of sensor panels 54 adapted to be disposed in overlapping sequence from adjacent the bed forward end 32 to adjacent the bed rear end 34, as described above and shown in FIG. 7. The sensor assembly 274 is adapted to lie generally flat upon the bed top surface 36, with the one of the left and right sensor panel edges having the circuit boards 70 extending outward and downward on the respective side of the frame 24. The sensor assembly 274 extends downward alongside the frame 24, and then curves upward with the circuit boards 70 disposed alongside the frame 24, as shown in FIG. 15. FIG. 17 shows the sensor panel edge having the circuit boards 70 extending outward on the left side of the treadmill 22 before installation.

Figure 7:
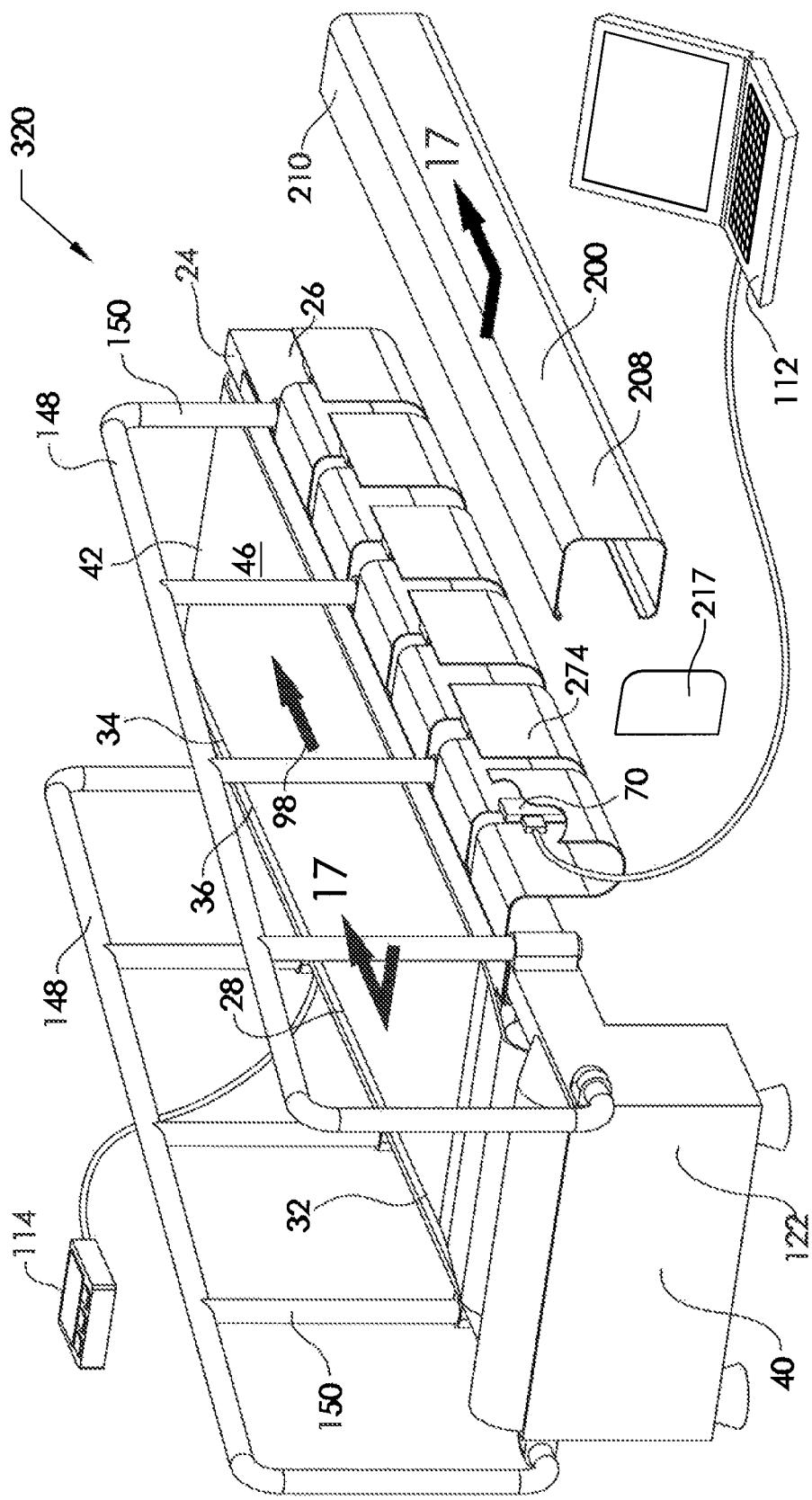
FIG. 7 is a perspective view of the canine gait analyzer of FIG. 1, mounted on the treadmill of FIG. 5, and showing the sensor panels installed on the treadmill with the circuit boards alongside the treadmill, and the side cover exploded away from the treadmill.

A side cover 200 has an upper flange 202 and a lower flange 204 connected by a web 206. The lower flange 204 is bent upward at the inside edge to fit against one of the frame left 26 and right 28 sides. The side cover 200 is generally C-shaped in cross-section, and extends between opposite front 208 and rear 210 ends. The side cover 200 is adapted to be attached to one of the frame left 26 and right 28 sides. The side cover 200 is adapted to cover the one of the left 62 and right 64 sensor panel edges having the circuit boards 70. The side cover lower flange 204 extends slightly underneath the treadmill frame 24. The side cover 200 will enclose, support and protect the sensor panel edges 62 or 64, as well as the circuit boards 70, which are now disposed upward and outboard of the treadmill frame 24. The side cover upper flange 202 includes a ridge 216 extending from the front 208 to the rear 210 end and projecting downward. The ridge 216 serves to hold down the edge of the sensor assembly 274 and to seal against RF (radio frequency) emissions. An end plate 217 on each end 208, 210, of the side cover 200 completes the RF shield. Only the front end plate 217 is shown in FIGS. 6 and 7, the rear end plate is not shown, but is similar and opposite-hand. Threaded fasteners (not shown) attach the side cover 200, and end plates 217 to the frame side 26 or 28, and ensure electrical continuity.

The J bracket 84 is the same as for canine gait analyzer 20 described above. A computer 112 is adapted to be connected to the circuit boards 70. A motor speed controller 114 is adapted to be connected to the motor (not shown) and to the computer 112. The circuit boards 70 are connected together in a similar manner to canine gait analyzer 20.

The canine gait analyzer 220 is assembled to the treadmill 22 by sliding the sensor assembly 74 transversely between the belt inner surface 44 and the bed top surface 36, as described for canine gait analyzer 20 above.

Referring now to FIG. 7, a canine gait analyzer is shown at 320, and is similar to the canine gait analyzer 220 described above. Canine gait analyzer 320 is used in connection with the treadmill 122 described above. A pair of guardrails 148 are mounted on the frame 24 by upright stanchions 150.

Typically, as before, a plurality of sensor panels 54 are employed, as shown in FIGS. 8-12. The peninsular portions 55 and cutout regions 61 and 63 of the sensor panels 54 are as described above. The cutout regions 61 and 63 and 65 clear the upright stanchions 150 on treadmill 122.

The side cover 200 will enclose, support and protect the sensor panel edges 62 or 64, as well as the circuit boards 70, which are disposed upward and outboard of the treadmill frame 24. The side cover 200 is the same as that of the canine gait analyzer 220 described above.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the structure may be varied substantially without departing from the spirit of the invention and the exclusive use of all modifications that will come within the scope of the appended claims is reserved.

PARTS LIST

Canine Gait Analyzer

Part
No. Description
20 canine gait analyzer
22 treadmill
24 treadmill frame
26 treadmill frame left side
28 treadmill frame right side
30 bed
32 bed forward end
34 bed rear end
36 bed top surface
38 rollers
40 treadmill forward end
42 belt
44 belt inner surface
46 belt outer surface
48 guardrail
50 guardrail front bushings
52 guardrail rear bushings
54 sensor panels
55 peninsular portions
56 flexible material
57 proximal end
58 sensor panels front
59 distal end
60 sensor panels rear
61 first cutout region
62 sensor panels left edge
63 second cutout region
64 sensor panels right edge
65 third cutout region
66 pressure transducer array
68 pressure transducers
70 circuit board
72 conductive traces
74 sensor assembly
75 flat ribbon cable
76 antifriction membrane
78 elastomer sheet
80 electrical ground
82 sensor assembly front end
84 J bracket
86 J bracket upper flange
88 J bracket lower flange
90 J bracket web
92 upper flange top surface
94 upper flange bottom surface
96 belt direction arrow
98 belt direction arrow
100 side cover
102 side cover upper flange
104 side cover lower flange
106 side cover web
108 side cover front end
110 side cover rear end
112 computer
114 motor speed controller
116 side cover ridge
117 end plate
118 seal plate
119 gasket
120 canine gait analyzer
122 treadmill
130 camera mounting bracket
132 camera
134 arm
136 leg
138 ball head
140 clamp base
142 clamp block
144 clamp jaw
148 guardrail
150 stanchions
220 canine gait analyzer
274 second sensor assembly
200 side cover
202 side cover upper flange
204 side cover lower flange
206 side cover web
208 side cover front end
210 side cover rear end
216 side cover ridge
217 end plate
320 canine gait analyzer

What is claimed is:

1. A canine gait analyzer, for use in connection with a treadmill having a frame, the frame having opposite left and right sides, a bed mounted on the frame, the bed extending between a forward end and a rear end, the bed having a top surface, front and rear rollers mounted on the frame, a belt mounted on the rollers, a motor driving one of the rollers, the belt having inner and outer surfaces, and a guardrail mounted on the frame, the canine gait analyzer comprising:

at least one sensor panel, the sensor panel having a portion of flexible material extending between opposite front and rear ends, and between opposite left and right edges, the sensor panel having a pressure transducer array received on the flexible material, the transducer array having a plurality of pressure transducers arranged in a matrix, the sensor panel having at least one circuit board adjacent one of the left and right edges, the circuit board including electronic components, the sensor panel having conductive traces connecting the pressure transducers electrically to the circuit board;

a sensor assembly including the at least one sensor panel, an antifriction membrane stacked above the sensor panel, and an elastomer sheet stacked adjacent the sensor panel, the sensor assembly having a front end, the sensor assembly being adapted for installation between the belt inner surface and the bed, the sensor assembly being adapted to lie generally flat upon the bed top surface, with the one of the left and right sensor panel edges having the circuit board extending outward and downward on the respective side of the frame;

an attaching member having opposite top and bottom surfaces, the attaching member being adapted to extend across the bed forward end with the belt passing over the top surface, the sensor assembly and the bed being attached to the attaching member, so that the attaching member will hold the sensor assembly disposed on the bed with the sensor assembly front end adjacent the bed forward end, wherein the belt will pass over the sensor assembly without moving the sensor assembly with respect to the bed; and a side cover extending between opposite front and rear ends, the side cover being adapted to be attached to one of the frame left and right sides, the side cover being adapted to cover the sensor panel edge having the circuit board, so as to protect the sensor panel edge and the circuit board.

2. The canine gait analyzer of claim 1, wherein the attaching member further comprises a J bracket having an upper flange and a lower flange connected by a web, the upper flange having opposite top and bottom surfaces, the J bracket being adapted to extend across the bed forward end with the upper flange above the bed and the lower flange below the bed and the web adjacent the bed forward end and the belt passing over the upper flange top surface, the sensor assembly being attached to the upper flange bottom surface, so that the J bracket will hold the sensor assembly disposed on the bed with the sensor assembly front end adjacent the bed forward end, wherein the belt will pass over the sensor assembly without moving the sensor assembly with respect to the bed.

3. The canine gait analyzer of claim 1, wherein the side cover includes an upper flange and a lower flange connected by a web, the side cover being generally C-shaped in cross-section, the side cover extending between opposite front and rear ends, the side cover being adapted to be attached to one of the frame left and right sides, the side cover being adapted to cover the sensor panel edge having the circuit board, so as to support and protect the sensor panel edge and the circuit board, the side cover including two end plates, the side cover and end plates being adapted to contain RF radiation when used in connection with the treadmill.

4. The canine gait analyzer of claim 1, wherein the sensor panel further comprises:
two peninsular portions extending outward from a proximal end adjacent one of the left and right edges to a distal end, the peninsular portions being separated by a first cutout region;
two circuit boards, each circuit board being mounted on one of the peninsular portions; and
a second cutout region adjacent one of the peninsular portions, the second cutout region extending outward from a proximal end adjacent one of the left and right edges to a distal end, and extending from one of the front and rear ends to one of the peninsular portions.

5. The canine gait analyzer of claim 4, wherein the peninsular portions are adapted to extend outward and downward on the side of the frame, and extend underneath the frame with the circuit boards disposed beneath the frame, with the side cover adapted to enclose and support the peninsular portions and the circuit boards.

6. The canine gait analyzer of claim 4, wherein the peninsular portions are adapted to extend outward and downward on the side of the frame, and extend upward alongside the frame with the circuit boards disposed alongside and outboard of the frame, with the side cover adapted to enclose and support the peninsular portions and the circuit boards.

7. The canine gait analyzer of claim 1, wherein the sensor assembly further comprises a plurality of sensor panels adapted to be disposed in overlapping sequence from adjacent the bed forward end to adjacent the bed rear end, the peninsular portions of the plurality of sensor panels all adapted to being disposed on the same side of the frame and extending outward and downward on the respective side of the frame.

8. The canine gait analyzer of claim 7, wherein
the elastomer sheet is stacked below the sensor panel, the elastomer sheet having carbon-graphite compounded therein so as to render the elastomer sheet conductive, the elastomer sheet adapted for being electrically grounded; and
attaching means for attaching the antifriction membrane and the elastomer sheet to the sensor panel,
so that upon assembling the canine gait analyzer to the treadmill, the sensor assembly will be transversely slidingly installed between the belt inner surface and the bed, and the sensor assembly will lie generally flat upon the bed top surface, and the elastomer sheet will be electrically grounded.

9. The canine gait analyzer of claim 7, wherein
the elastomer sheet is stacked above the sensor panel, the elastomer sheet having carbon-graphite compounded therein so as to render the elastomer sheet conductive, the elastomer sheet adapted for being electrically grounded; and
attaching means for attaching the antifriction membrane and the elastomer sheet to the sensor panel,
so that upon assembling the canine gait analyzer to the treadmill, the sensor assembly will be transversely slidingly installed between the belt inner surface and the bed, and the sensor assembly will lie generally flat upon the bed top surface, and the elastomer sheet will be electrically grounded.

10. The canine gait analyzer of claim 1, further comprising:
a computer adapted to be connected to the at least one circuit board;
a motor speed controller adapted to be connected to the motor and to the computer; and
a camera mounting bracket for attaching a video camera.

11. A canine gait analyzer, for use in connection with a treadmill having a frame, the frame having opposite left and right sides, a bed mounted on the frame, the bed extending between a forward end and a rear end, the bed having a top surface, front and rear rollers mounted on the frame, a belt mounted on the rollers, a motor driving one of the rollers, the belt having inner and outer surfaces, and a guardrail mounted on the frame, the canine gait analyzer comprising:

a plurality of sensor panels, the sensor panels each having a portion of flexible material extending between opposite front and rear ends, and between opposite left and right edges, the sensor panels each having a pressure transducer array received on the flexible material, the transducer array having a plurality of pressure transducers arranged in an orthogonal matrix, each one of the plurality of sensor panels having at least one circuit board adjacent one of the left and right edges, the circuit board including electronic components, each sensor panel having conductive traces connecting the pressure transducers electrically to the circuit board;

a sensor assembly including the plurality of sensor panels adapted to be disposed in overlapping sequence from adjacent the bed forward end to adjacent the bed rear end, an antifriction membrane stacked above the sensor panels, and an elastomer sheet stacked adjacent the sensor panels, the sensor assembly having a front end, the sensor assembly being adapted for installation between the belt inner surface and the bed, the sensor assembly being adapted to lie generally flat upon the bed top surface, with the one of the left and right sensor panel edges having the circuit board extending outward and downward on the respective side of the frame;

a J bracket having an upper flange and a lower flange connected by a web, the upper flange having opposite top and bottom surfaces, the J bracket being adapted to extend across the bed forward end with the upper flange above the bed and the lower flange below the bed and the web adjacent the bed forward end and the belt passing over the upper flange top surface, the sensor assembly being attached to the upper flange bottom surface, so that the J bracket will hold the sensor assembly disposed on the bed with the sensor assembly front end adjacent the bed forward end, wherein the belt will pass over the sensor assembly without moving the sensor assembly with respect to the bed; and a side cover having an upper flange and a lower flange connected by a web, the side cover being generally C-shaped in cross-section, the side cover extending between opposite front and rear ends, the side cover being adapted to be attached to one of the frame left and right sides, the side cover being adapted to cover the one of the left and right sensor panel edges having the circuit board, so as to support and protect the sensor panel edges and the circuit board, the side cover including two end plates, the side cover and end plates being adapted to contain RF radiation when used in connection with the treadmill.

12. The canine gait analyzer of claim 11, wherein each of the sensor panels further comprises:

two peninsular portions extending outward from a proximal end adjacent one of the left and right edges to a distal end, the peninsular portions being separated by a first cutout region;

two circuit boards, each circuit board being mounted on one of the peninsular portions; and a second cutout region adjacent one of the peninsular portions, the second cutout region extending outward from a proximal end adjacent one of the left and right edges to a distal end, and extending from one of the front and rear ends to one of the peninsular portions.

13. The canine gait analyzer of claim 12, wherein the peninsular portions are adapted to extend outward and downward on the side of the frame, and extend underneath the frame with the circuit boards disposed beneath the frame, with the side cover adapted to enclose and support the peninsular portions and the circuit boards.

14. The canine gait analyzer of claim 12, wherein the peninsular portions are adapted to extend outward and downward on the side of the frame, and extend upward alongside the frame with the circuit boards disposed alongside and outboard of the frame, with the side cover adapted to enclose and support the peninsular portions and the circuit boards.

15. The canine gait analyzer of claim 11, wherein the elastomer sheet is stacked below the sensor panel, the elastomer sheet having carbon-graphite compounded therein so as to render the elastomer sheet conductive, the elastomer sheet adapted for being electrically grounded; and attaching means for attaching the antifriction membrane and the elastomer sheet to the sensor panel, so that upon assembling the canine gait analyzer to the treadmill, the sensor assembly will be transversely slidingly installed between the belt inner surface and the bed, and the sensor assembly will lie generally flat upon the bed top surface, and the elastomer sheet will be electrically grounded.

16. The canine gait analyzer of claim 11, wherein the elastomer sheet is stacked above the sensor panel, the elastomer sheet having carbon-graphite compounded therein so as to render the elastomer sheet conductive, the elastomer sheet adapted for being electrically grounded; and attaching means for attaching the antifriction membrane and the elastomer sheet to the sensor panel, so that upon assembling the canine gait analyzer to the treadmill, the sensor assembly will be transversely slidingly installed between the belt inner surface and the bed, and the sensor assembly will lie generally flat upon the bed top surface, and the elastomer sheet will be electrically grounded.

17. The canine gait analyzer of claim 11, further comprising:

a computer adapted to be connected to the at least one circuit board;

a motor speed controller adapted to be connected to the motor and to the computer; and a camera mounting bracket for attaching a video camera.

18. A canine gait analyzer, for use in connection with a treadmill having a frame, the frame having opposite left and right sides, a bed mounted on the frame, the bed extending between a forward end and a rear end, the bed having a top surface, front and rear rollers mounted on the frame, a belt mounted on the rollers, a motor driving one of the rollers, the belt having inner and outer surfaces, and a guardrail mounted on the frame, the canine gait analyzer comprising:

a plurality of sensor panels, the sensor panels each having a portion of flexible material extending between opposite front and rear ends, and between opposite left and right edges, the sensor panels each having a pressure transducer array received on the flexible material, the transducer array having a plurality of pressure transducers arranged in an orthogonal matrix, each one of the plurality of sensor panels having two circuit boards adjacent one of the left and right edges, each circuit board including electronic components, each sensor panel having conductive traces connecting the pressure transducers electrically to the circuit boards;

a sensor assembly including the plurality of sensor panels adapted to be disposed in overlapping sequence from adjacent the bed forward end to adjacent the bed rear end, an antifriction membrane stacked above the sensor panels, and an elastomer sheet stacked adjacent the sensor panels, the elastomer sheet having carbon-graphite compounded therein so as to render the elastomer sheet conductive, the elastomer sheet adapted for being electrically grounded, the sensor assembly having a front end, the sensor assembly being adapted for installation between the belt inner surface and the bed, the sensor assembly being adapted to lie generally flat upon the bed top surface, with the one of the left and right sensor panel edges having the circuit boards extending outward and downward on the respective side of the frame;

attaching means for attaching the antifriction membrane and the elastomer sheet to the sensor panels;

a J bracket having an upper flange and a lower flange connected by a web, the upper flange having opposite top and bottom surfaces, the J bracket being adapted to extend across the bed forward end with the upper flange above the bed and the lower flange below the bed and the web adjacent the bed forward end and the belt passing over the upper flange top surface, the sensor assembly being attached to the upper flange bottom surface, so that the J bracket will hold the sensor assembly disposed on the bed with the sensor assembly front end adjacent the bed forward end, wherein the belt will pass over the sensor assembly without moving the sensor assembly with respect to the bed;

a side cover having an upper flange and a lower flange connected by a web, the side cover being generally C-shaped in cross-section, the side cover extending between opposite front and rear ends, the side cover being adapted to be attached to one of the frame left and right sides, the side cover being adapted to cover the one of the left and right sensor panel edges having the circuit boards, so as to support and protect the sensor panel edges and the circuit boards, the side cover including two end plates, the side cover and end plates being adapted to contain RF radiation when used in connection with the treadmill;

a computer adapted to be connected to the circuit boards; and a motor speed controller adapted to be connected to the motor and to the computer, so that upon assembling the canine gait analyzer to the treadmill, the sensor assembly will be transversely slidingly installed between the belt inner surface and the bed, the J bracket will engage the bed forward end, the sensor assembly will lie generally flat upon the bed top surface, the elastomer sheet will be electrically grounded, the computer will be connected to the circuit boards, and the motor speed controller will be connected to the motor and to the computer.

19. The canine gait analyzer of claim 18, wherein the sensor panel edges having the circuit boards are adapted to extend outward and downward on the side of the frame, and extend underneath the frame with the circuit boards disposed beneath the frame, with the side cover adapted to enclose and support the sensor panel edges and the circuit boards.

20. The canine gait analyzer of claim 18, wherein the sensor panel edges having the circuit boards are adapted to extend outward and downward on the side of the frame, and extend upward alongside the frame with the circuit boards disposed alongside and outboard of the frame, with the side cover adapted to enclose and support the sensor panel edges and the circuit boards.

* * * * *